United States Patent [19]

Kissener et al.

[11] Patent Number: 5,145,958
[45] Date of Patent: Sep. 8, 1992

[54] PROCESS FOR THE PREPARATION OF 2,4- OR 2,6-DIHALOGENO-ANILINE

[75] Inventors: Wolfram Kissener, Bergisch-Gladbach; Helmut Fiege, Leverkusen, both of Fed. Rep. of Germany

[73] Assignee: Bayer Aktiengesellschaft, Leverkusen, Fed. Rep. of Germany

[21] Appl. No.: 799,918

[22] Filed: Nov. 26, 1991

Related U.S. Application Data

[63] Continuation of Ser. No. 581,837, Sep. 12, 1990, abandoned.

[30] Foreign Application Priority Data

Oct. 4, 1989 [DE] Fed. Rep. of Germany ....... 3933093

[51] Int. Cl.$^5$ ............................................ C07C 209/78
[52] U.S. Cl. ........................... 544/106; 544/172; 544/395; 546/192; 546/238; 548/572; 548/577; 560/47; 564/393; 564/394; 564/412; 564/413; 564/442
[58] Field of Search ............... 564/393, 394, 412, 413, 564/442; 546/192, 238; 548/572, 577; 560/47; 544/106, 175, 395

[56] References Cited

U.S. PATENT DOCUMENTS

| | | | |
|---|---|---|---|
| 3,801,636 | 4/1974 | Harrom | 564/442 |
| 4,182,877 | 1/1980 | Harris et al. | 564/393 |
| 4,447,647 | 5/1984 | Werner et al. | 564/412 |

FOREIGN PATENT DOCUMENTS 0056629 7/1982 .
083442 7/1983 European Pat. Off. ............ 564/412
55-35017 3/1980 Japan .

OTHER PUBLICATIONS

Acharya et al., *Chem Abs.* 84: 164351a, 1976.
Liebenow, et al., *Chem Abs.* 103: 37181f, 1985.
Cirera et al., *Chem Abs.* 104: 109177e, 1986.
Organic Synthesis, vol. 24, pp. 47-53 John Wiley & Sons, Inc., New York, (1945).
Receuil Des Travaux Chimiques Des Pays-Bas, vol. 78, No. 7, pp. 534-542 C. Van Det Stelt et al. (1959).
Chemical Abstracts, vol. 97, No. 19, p. 675 (1982).

*Primary Examiner*—Carolyn Elmore
*Assistant Examiner*—Scott C. Rand
*Attorney, Agent, or Firm*—Sprung Horn Kramer & Woods

[57] ABSTRACT

2,4- or 2,6-dihalogeno-aniline can be prepared by reacting an amino-benzoic acid ester of the formula

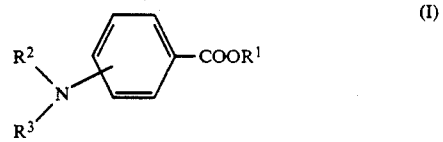

(I)

in which $R^1$, $R^2$ and $R^3$ have the meanings indicated in the description, with 2-2.5 moles of a chlorinating or brominating agent in an inert reaction medium at a temperature of 40°-160° C. and subsequently hydrolyzing and decarboxylating the dihalogenated amino-benzoic acid ester.

18 Claims, No Drawings

PROCESS FOR THE PREPARATION OF 2,4- OR 2,6-DIHALOGENO-ANILINE

This application is a continuation of application Ser. No. 581,837 filed Sep. 12, 1990 now abandoned.

BACKGROUND OF THE INVENTION

1. Field of the Invention

The present invention relates to a process for the preparation of 2,4- or 2,6-dihalogeno-aniline by reaction of an amino-benzoic acid ester with a chlorinating or brominating agent and subsequent hydrolysis and decarboxylation.

2,4- or 2,6-dichloro- and dibromo-aniline are important intermediates for the preparation of medicaments, dyes and plant protection agents.

2. Description of the Related Art

It is known to prepare 2,6-dichloroaniline in a two-step process by reaction of sulphanilamide with the equivalent amount of 30% strength hydrogen peroxide in half-concentrated hydrochloric acid at 60° C. and subsequent hydrolysis of the 3,5-dichlorosulphanilamide thus obtained in 70% strength sulphuric acid at 165°-195° C. (Org. Synt. Coll. Vol. III (1955), 262). However, the product prepared in this way is not pure and requires purification before being used for further synthesis steps. According to DD 64,061, this process is revised by intermediate isolation of the chlorinated sulphanilamide; however, the yield of 62.5% over both process steps is unsatisfactorily low. In DD 247,670, a further process for the preparation of 2,6-dichloroaniline is described, which also starts from sulphanilamide. In this process, 2,4,6-trichloroaniline is obtained at the same time and isolated; however, the yield of pure 2,6-dichloroaniline is also low.

Another method of preparation of 2,6-dichloroaniline is described in ES 503,386, cited by C.A. 97 (1982), 162,558 t. In this case, 3,5-dichloro-4-amino-benzoic acid is reacted with potassium bromate to give 3,5-dichloro-4-bromoaniline and then reduced with zinc in alkaline solution. The preparation of pure 3,5-dichloro-4-amino-benzoic acid as the starting material is only possible, however, in poor yields (Rec. 78 (1959) 534 and Chem. Ber. 74 (1941), 807).

In JP Patent Application 57/169,447 (1982), the preparation of 2,6-dichloroaniline is described starting from 3,5-dichloro-bromobenzene, which is nitrated and hydrogenated catalytically with hydrogen to give aniline. Since the nitro group can occur in the p- and o-position to the bromine, a mixture of 2,6- and 2,4-dichloroaniline is obtained.

SUMMARY OF THE INVENTION

A process for the preparation of 2,4- or 2,6-dihalogeno-aniline has now been found, which is characterized in that an amino-benzoic acid ester of the formula

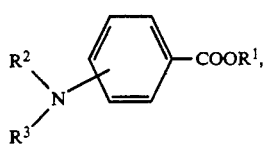

in which $R^1$ denotes straight-chain or branched $C_1$-$C_8$-alkyl, benzyl or phenyl and $R^2$ and $R^3$, independently of one another, represent hydrogen, straight-chain or branched $C_1$-$C_8$-alkyl or benzyl, where $R^2$ and $R^3$ together may denote —(—CH$_2$—)$_4$—, —(—CH$_2$—)$_5$—, —C$_2$H$_4$—O—C$_2$H$_4$—, —C$_2$H$_4$—NH—C$_2$H$_4$—, or —C$_2$H$_4$—NCH$_3$—C$_2$H$_4$—, is reacted with 2-2.5 moles of a chlorinating or brominating agent in an inert reaction medium at a temperature of 40°-160° C. and the dihalogenated amino-benzoic acid ester is subsequently hydrolyzed and decarboxylated.

DETAILED DESCRIPTION OF THE INVENTION

Straight-chain or branched $C_1$-$C_8$-alkyl is, for example, methyl, ethyl, propyl, isopropyl, butyl, isobutyl, tert.-butyl, the isomeric amyls, hexyls, or octyls. Of these, the $C_1$-$C_4$-alkyl radicals mentioned are preferred; ethyl and isobutyl are particularly preferred.

Benzyl in the aromatic moiety or phenyl may be substituted by $C_1$-$C_4$-alkyl of the type mentioned, preferably by methyl, and also by fluorine, chlorine or bromine or by $C_1$-$C_4$-alkoxy, preferably by methoxy.

The N atom of the amino group can be substituted in the manner mentioned.

In a preferred manner, 4-amino-benzoic acid esters of the formula

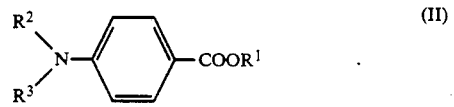

are employed in which $R^1$, $R^2$ and $R^3$ have the above-mentioned meaning.

In a furthermore preferred manner, amino-benzoic acid esters of the formulae (I) and (II) are employed in which the radical $R^{11}$ having the meaning of a straight-chain or branched $C_1$-$C_4$-alkyl or phenyl occurs in place of $R^1$. In a particularly preferred manner, amino-benzoic acid esters of the formulae (I) and (II) are employed in which the radical $R^{21}$ having the meaning of a straight-chain or branched $C_1$-$C_4$-alkyl radical occurs in place of $R^{11}$.

In a furthermore preferred manner, amino-benzoic acid esters of the formulae (I) and (II) are employed in which the radicals $R^{12}$ and $R^{13}$, of which $R^{12}$ denotes hydrogen, straight-chain or branched $C_1$-$C_4$-alkyl or benzyl and $R^{13}$ represents hydrogen, methyl or ethyl, occur in place of $R^2$ and $R^3$. In a particularly preferred manner, amino-benzoic acid esters of the formulae (I) and (II) are employed in which the radical $R^{22}$ having the meaning of hydrogen, methyl or ethyl occurs in place of $R^{12}$ and in which hydrogen occurs in place of $R^{13}$.

Examples of amino-benzoic acid esters which can be employed according to the invention are methyl 4-amino-benzoate, ethyl 4-amino-benzoate, isopropyl 4-amino-benzoate, isobutyl 4-amino-benzoate and phenyl 4-amino-benzoate.

The preparation of amino-benzoic acid esters of the type mentioned can be carried out in a manner known to the person skilled in the art, for example by esterification of nitrobenzoic acid with an alcohol or with phenol and subsequent hydrogenation or by esterification of 4-aminobenzoic acid. The amino group may furthermore be alkylated with the above radicals R² and R³ in a known manner (compare Houben-Weyl, Methoden der Organischen Chemie (Methods of Organic Chemistry) VIII (1952), 516 and XI/1 (1957), 360).

In the case of amino-benzoic acid esters having an amino group in the p-position, 2,6-dihalogeno-aniline is accordingly obtained. In the case of an amino group in the o-position, 2,4-dihalogeno-aniline is obtained. In the case of an amino group in the m-position, essentially 2,6-dihalogeno-aniline is obtained in addition to some 2,4-dihalogeno-aniline. The process according to the invention is most important for the reaction of amino-benzoic acid esters having an amino group in the p-position.

The 2,4- or 2,6-dihalogeno-anilines obtainable according to the invention are accordingly those of the formulae

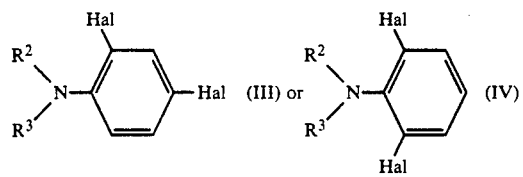

in which
R² and R³ have the above meaning and
Hal represents chlorine or bromine.

Examples of chlorinating or brominating agents which may be mentioned are chlorine, sulphuryl chloride, hydrogen chloride/hydrogen peroxide, bromine, sulphuryl bromide or hydrogen bromide/hydrogen peroxide, preferentially chlorine or bromine.

These chlorinating or brominating agents are employed in an amount of from 2-2.5 moles, preferably 2-2.1 moles, particularly preferably 2-2.05 moles, per mole of the amino-benzoic acid ester. In a furthermore preferred manner, the halogenation is a chlorination.

Suitable inert reaction media are aliphatic or aromatic halogenohydrocarbons, such as chlorobenzene, dichlorobenzene, carbon tetrachloride, bromobenzene or the like, which are known for such purposes to the person skilled in the art. The inert reaction medium may also consist of several solvents/diluents of the type mentioned. The inert reaction medium is employed in an amount of 50-3,000, preferably 100-1,500, particularly preferably 300-1,000 ml, per mole of the amino-benzoic acid ester.

The chlorination or bromination according to the invention is carried out at a temperature of 40°-160° C., preferably 60°-140° C., particularly preferably 70°-110° C.

The chlorination or bromination reaction can be carried out, for example, in such a way that the amino-benzoic acid ester is initially introduced into the inert reaction medium, after which the reaction mixture is brought to the selected reaction temperature with stirring. Should the selected reaction temperature be above the boiling point of the reaction medium, the reaction can be carried out at elevated pressure in a manner known to the person skilled in the art. Otherwise, the process according to the invention is independent of the pressure. The chlorinating agent is then introduced at the selected reaction temperature, most favourably at the rate at which it is consumed. After blowing out the remainder of the halogenating agent and its reaction products, the reaction products can be isolated by merely distilling off the reaction medium. However, it is also possible to introduce the inert reaction medium initially and to introduce the amino-benzoic acid ester and the halogenating agent simultaneously; in this variant a part of the amino-benzoic acid ester can also be initially introduced, while the rest is introduced simultaneously to the halogenating agent. Such a simultaneous introduction may also be begun even before attaining the selected reaction temperature; the reaction temperature is then still attained during the simultaneous introduction by warming the reaction mixture.

In the halogenation, a catalyst such as FeCl₃, TiCl₄ or ZnCl₂ can basically be employed. However, such catalysts offer no other advantage, and it is even a particular feature of the halogenation according to the invention that it can be carried out without such catalysts.

It is a further particular feature of the halogenation according to the invention that it can also be carried out on substrates of the formula (I) or (II) in which one or both radicals R² and R³ assume the meaning of hydrogen without an undesired n-halogenation occurring, which usually has to be prevented by protective groups, such as an acetyl group, which subsequently only has to be removed again in a separate reaction step.

The doubly chlorinated or brominated amino-benzoic acid ester is then hydrolyzed and decarboxylated.

In this connection, a process can be used in which the doubly chlorinated or brominated amino-benzoic acid ester is hydrolyzed to give the carboxylic acid on which it is based under alkaline or acid conditions in a manner basically known to the person skilled in the art. This carboxylic acid is subsequently decarboxylated at 100°-400° C., preferably 150°-300° C., particularly preferably 180°-280° C., in a solvent/diluent which is inert with respect to the decarboxylation.

Solvents/diluents may be polar organic compounds, organic or inorganic acids and water. Examples of these are: dimethylformamide, sulpholane, dimethyl sulphoxide, acetic acid, hydrochloric acid, sulphuric acid; the reaction is preferentially carried out in water. Such solvents/diluents or a mixture of several of them are employed in an amount of 50-2,000, preferably 200-1,500, particularly preferably 500-1,300 ml, per mole of the doubly chlorinated or brominated amino-benzoic acid.

This decarboxylation is basically independent of the pressure. An elevated pressure is therefore only used if the selected working temperature is above the boiling point of the solvent/diluent. In such a case the reaction can be carried out, for example, in a stirring autoclave under the pressure which is automatically established.

In the case in which the doubly chlorinated or brominated amino-benzoic acid is liquid at the selected working temperature, a solvent/diluent may also be basically dispensed with. In the sense of a uniform course of the reaction, however, it is preferred to use a solvent/diluent of the above type and in the above amount.

Basically, it is possible to carry out the decarboxylation in the presence of acid-reacting compounds, for example Brönstedt or Lewis acids, bleaching earths or acid-reacting ion exchangers or zeolites, as long as the selected solvent/diluent is not an acid itself. However, as it is also basically possible to work in the presence of a non-acidic solvent/diluent, such an addition is unnecessary and is preferably omitted owing to the simplified working up.

After the decarboxylation, the 2,4- or 2,6-dichloro(bromo)aniline can be recovered from the decarboxylation mixture by crystallization, solvent extraction, distillation or steam distillation.

The smooth course of the decarboxylation in high space-time yields and with the attainment of high purity is surprising, since it is known that the decarboxylation of non-activated aromatic carboxylic acids requires very high reaction temperatures, long reaction times or additions of catalysts, such as metal salts (Houben-Weyl, Vol. E5 (1985), 468 and Vol. VIII (1952), 494; EP 55,629).

In an advantageous manner, however, the hydrolysis and decarboxylation can be carried out in one step. For this purpose, the reaction is carried out in water or a water-containing solvent/diluent at 100°–400° C., preferably 150°–300° C., particularly preferably 180°–280° C.

Suitable solvents/diluents which can be used with water are aliphatic or aromatic hydrocarbons, aliphatic or aromatic halogenohydrocarbons or organic or inorganic acids. Examples of such solvents/diluents to be employed together with water are: toluene, chlorobenzene, acetic acid, hydrochloric acid and sulphuric acid. Preferentially, however, the reaction is carried out in water alone, the advantage of simplified working up of the reaction mixture presenting itself. An addition of very small amounts of acid to establish a pH of 4–6.5 may be desirable; however, it is basically possible to dispense with all such additions. Water or a water-containing solvent/diluent is employed in an amount of 50–2,000, preferably 200–1,500, particularly preferably 500–1,300 ml, per mole of the doubly chlorinated or brominated amino-benzoic acid ester.

In the case of the preferred simultaneous hydrolysis and decarboxylation in water, pressure is necessary in order to attain the reaction temperature and to prevent water from distilling off. This pressure is preferentially the intrinsic pressure of the system which is established by itself in a manner known to the person skilled in the art. Basically, it is possible to apply an additional pressure by means of an inert gas, such as nitrogen, hydrogen, rare gases or the like; as a rule, these are dispensed with for reasons of simplicity. The initial pressure increases owing to the cleavage products of the hydrolysis and decarboxylation. This elevated pressure can be reduced by partial depressurization.

The working up of such a hydrolysis and decarboxylation mixture takes place in the manner described above.

EXAMPLE 1

1 mole = 151 g of methyl 4-amino-benzoate were initially introduced in 1 l of chlorobenzene. The mixture was heated to 100° C. and 2 mole = 142 g of chlorine were introduced at this temperature over the course of four hours. The solvent was subsequently distilled off in vacuo. 221 g of methyl 3,5-dichloro-4-amino-benzoate remained, corresponding to a yield of 92.4%.

0.2 mole = 48 g of methyl 3,5-dichloro-4-amino-benzoate were initially introduced into an autoclave together with 250 ml of water. The mixture was heated to 250° C. and stirred at this temperature for 3 hours. Reaction gas formed was continuously let off to maintain a pressure of about 40 bar. The product was recovered by steam distillation. 26.9 g of 2,6-dichloroaniline were obtained, corresponding to a yield of 75.3%.

EXAMPLE 2

1 mole = 165 g of ethyl 4-amino-benzoate were initially introduced in 1 l of chlorobenzene. The mixture was heated to 100° C. and 2 mole = 142 g of chlorine were introduced over the course of three hours. The solvent was completely distilled off in vacuo and 232 g of ethyl 3,5-dichloro-4-amino-benzoate remained, corresponding to a yield of 94%.

0.2 mole = 49.3 g of ethyl 3,5-dichloro-4-amino-benzoate were initially introduced into an autoclave together with 250 ml of water. The mixture was heated to 250° C. and stirred at this temperature for 2.5 hours. Reaction gas formed was continuously removed to maintain a pressure of about 40 bar. The product was subsequently recovered by steam distillation. 31 g of 2,6-dichloroaniline were obtained, corresponding to a yield of 94%.

EXAMPLE 3

1 mole = 194 g of isobutyl 4-amino-benzoate were initially introduced in 1 l of chlorobenzene. The mixture was heated to 90° C. and 2 mole = 142 g of chlorine were introduced at this temperature over the course of four hours. After distilling off the solvent in vacuo, 260 g of isobutyl 3,5-dichloro-4-amino-benzoate remained, corresponding to a yield of 94%.

0.2 mole = 55.2 g of isobutyl 3,5-dichloro-4-amino-benzoate were initially introduced into an autoclave together with 250 ml of water. The mixture was stirred at 250° C. for 2.5 hours and the reaction gas formed was continuously removed to maintain a pressure of about 40 bar. The product was recovered by steam distillation. 32 g of 2,6-dichloroaniline were obtained, corresponding to a yield of 98%.

EXAMPLE 4

49 g (0.174 mole) of phenyl 3,5-dichloro-4-amino-benzoate were initially introduced into an autoclave together with 200 ml of water. The mixture was heated to 250° C. and stirred at this temperature for eight hours. During the reaction, the reaction gas was let off continuously and a pressure of about 41 bar was established. The residue was steam-distilled, and 35.8 g of 2,6-dichloroaniline having a purity of 63% were obtained. This corresponds to a yield of 80%.

EXAMPLE 5

0.2 mole = 41.2 g 3,5-dichloro-4-amino-benzoate were initially introduced into an autoclave together with 250 ml of water. The mixture was heated to 250° C. and stirred at this temperature for eight hours. The product was then recovered by steam distillation. 26 g of 2,6-dichloroaniline were obtained in a purity of 99.8%, corresponding to a yield of 80%.

What is claimed is:

1. A process for the preparation of 2,4- or 2,6-dichloro aniline, wherein an amino-benzoic acid ester of the formula

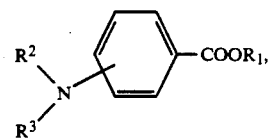

in which $R^1$ denotes straight-chain or branched $C_1$-$C_8$-alkyl, benzyl or phenyl and $R^2$ and $R^3$, independently of one another, represent hydrogen, straight-chain or branched $C_1$-$C_8$-alkyl or benzyl, where $R^2$ and $R^3$ together may denote —(—$CH_2$—)$_4$, —(—$CH_2$—)$_5$, —$C_2$—$H_4$—O—$C_2H_4$—, —$C_2H_4$—NH—O—$C_2H_4$—, or —$C_2H_4$—$NCH_3$—$C_2H_4$—, is reacted with 2-2.5 moles of elementary chlorine in an aromatic halogeno hydrocarbon at a temperature of 40°-160° C. thereafter distilling off the aromatic halogeno hydrocarbon and subsequently hydrolyzing and decarboxylating the dichlorinated amino-benzoic acid ester which is obtained.

2. The process of claim 1, wherein as an amino-benzoic acid ester, one of the formula

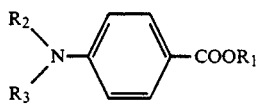

is employed in which $R^1$, $R^2$ and $R^3$ have the meaning mentioned in claim 1.

3. The process of claim 1, wherein the radical $R^{11}$ having the meaning of a straight-chain or branched $C_1$-$C_4$-alkyl or phenyl replaces $R^1$.

4. The process of claim 3, wherein the radical $R^{21}$ having the meaning of straight-chain or branched $C_1$-$C_4$-alkyl replaces $R^{11}$.

5. The process of claim 1, wherein the radicals $R^{12}$ and $R^{13}$ replace $R^2$ and $R^3$, respectivly, of which $R^{12}$ denotes hydrogen, straight-chain or branched $C_1$-$C_4$-alkyl or benzyl and $R^{13}$ respents hydrogen, methyl or ethyl.

6. The process of claim 5, wherein the radical $R^{22}$ having the meaning of hydrogen, methyl or ethyl replaces $R^{12}$, and hydrogen occurs in place of $R^{13}$.

7. The process of claim 1, wherein the doubly chlorinated or brominated amino-benzoic acid ester is hydrolyzed to give the carboxylic acid on which it is based under alkaline or acid conditions and this carboxylic acid is subsequently decarboxylated at 100°-400° C. in a solvent/diluent which is inert with respect to the decarboxylation.

8. The process of claim 7, wherein the decarboxylation is carried out at 150°-300° C.

9. The process of claim 8, wherein the decarboxylation is carried out at 180°-280° C.

10. The process of claim 7, which is carried at in dimethylformamide, sulpholane, dimethyl sulphoxide, acetic acid, hydrochloric acid, sulphuric acid, water or a mixture thereof in an amount of 50-2,000 ml per mole of the carboxylic acid.

11. The process of claim 10, which is carried out in water.

12. The process of claim 10, wherein 200-1,500 ml of the solvent/diluent per mole of the carboxylic acid are used.

13. The process of claim 12, wherein 500-1,300 ml of the solvent/diulent per mole of the carboxylic acid are used.

14. The process of claim 1, wherein the hydrolysis and decarboxylation are carried out in one step in water or a water-containing solvent/diluent at 100°-400° C.

15. The process of claim 14, wherein a temperature of from 150°-300° C. is used.

16. The process of claim 15, wherein a temperature of from 180°-280° C. is used.

17. The process of claim 1, wherein the elementary chlorine is used in an amount of 2-2.1 moles per mole of the amino-benzoic acid ester.

18. The process of claim 17, wherein the elementary chlorine is used in an amount of 2-2.05 moles per mole of the amino-benzoic acid ester.

* * * * *